(12) United States Patent
Hanson et al.

(10) Patent No.: US 8,562,950 B2
(45) Date of Patent: Oct. 22, 2013

(54) GABA BIOMARKERS FOR DEPRESSION

(75) Inventors: Peter Hanson, Newcastle upon Tyne (GB); Duncan Hiscock, Amersham (GB); Chris Morris, Newcastle upon Tyne (GB); Alan Thomas, Newcastle upon Tyne (GB)

(73) Assignee: GE Healthcare Limited, Little Chalfont (GB)

( * ) Notice: Subject to any disclaimer, the term of this patent is extended or adjusted under 35 U.S.C. 154(b) by 358 days.

(21) Appl. No.: 12/991,925

(22) PCT Filed: May 15, 2009

(86) PCT No.: PCT/EP2009/055944
§ 371 (c)(1),
(2), (4) Date: Nov. 10, 2010

(87) PCT Pub. No.: WO2009/138500
PCT Pub. Date: Nov. 19, 2009

(65) Prior Publication Data
US 2011/0091381 A1    Apr. 21, 2011

(30) Foreign Application Priority Data

May 15, 2008   (GB) .................................. 0808832.0

(51) Int. Cl.
*A61K 49/00*    (2006.01)
(52) U.S. Cl.
USPC .......................................... 424/9.1; 600/436
(58) Field of Classification Search
None
See application file for complete search history.

(56) References Cited

U.S. PATENT DOCUMENTS

| 2005/0130203 A1 | 6/2005 | Liu et al. |
| 2006/0051786 A1 | 3/2006 | Akil et al. |

FOREIGN PATENT DOCUMENTS

| WO | 02/20492 | 3/2002 |
| WO | 2008/020435 | 2/2008 |

OTHER PUBLICATIONS

Ghose et al., British Journal of Pharmacology (2011) vol. 162, pp. 1-17.*
Vischer et al., British Journal of Pharmacology (2011) vol. 163, pp. 246-260.*
Kugaya, et.al. "Cerebral Benzodiazepine Receptors in Depressed Pateients Measured With [123I]Iomazenil Spect." Biological Psychiatry Oct. 15, 2003, vol. 54, No. 8, pp. 792-799.
Smith, eta.l. "Molecular Tools for Assessing Human Depression by Positron Emission Tomography." European Neuropsychopharmacology: The Journal of the European College of Neuropsychopharmacology Sep. 2009, vol. 19. No. 9. pp. 611-628.
Hoepping, et.al. "Syntesis of Fluorine Substituted Pyrazolopyrimidines as Potential Leads for the Development of Pet-Imaging Agents for the Gabaa Receptors" Bioorganic & Medicinal Chemistry, Elsevier Science Ltd., GB. vol. 16, No. 3, Nov. 26, 2007, pp. 1184-1194.
Pimlott "Radiotracer Development in Psychiatry" Nuclear Medicine Communications Mar. 2005, vol. 26, No. 3, pp. 183-188.
Derry, et.al. "Identification of a Residue in the Gamma-Aminobutyric Acid Type A Receptor Alpha Subunit That Differentially Affects Diazepam-Sensitive and -Insensitive Benzodiazepine Site Binding" Journal of Neurochemistry Mar. 2004, vol. 88, No. 6, pp. 1431-1438.
Brambilla, et.al. "Gabaergic Dysfunction in Mood Disorders" Molecular Psychiatry Aug. 2003, vol. 8, No. 8, pp. 721-737.
Sanacora, et.al. "Impairment of Gabaergic Transmission in Depression: New Insights From Neuroimaging Studies" Critical Reviews in Neurobiology, CRC Press, Boca Raton, FL. vol. 14, No. 2, Jan. 1, 2000, pp. 23-45.
Smith, et.al. "The Use of Singe Photon Emission Computed Tomography in Depressive Disorders" Nuclear Medicine Communications, Lippincott Williams and Wilkins, XX, vol. 26, No. 3, Mar. 1, 2005, pp. 197-203.
Vaishnavi, et.al. "Neuroimaging in Late-Life Depression" International Review of Psychiatry, Carfax, Abingdon, GB., vol. 18, No. 5, Oct. 1, 2006, pp. 443-451.
Gareri, et.al. "Conventional and New Antidepressant Drugs in the Elderly." Progress in Neurobiology Jul. 2000, vol. 61, No. 4, pp. 353-396.
Hasler, et.al. "Reduced Prefrontal Glutamate/Glutamine and Gamma-Aminobutyric Acid Levels in Major Depression Determined Using Proton Magnetic Resonance Spectroscopy" Achrives of General Psychiatry Feb. 2007, vol. 64, No. 2, pp. 193-200.
Sanacora, et.al. "Gabaergic Contributions to the Pathophysiology of Depression and the Mechanism of Antidepressant Action." CNS & Neurological Disorders Drug Targets Apr. 2007, vol. 6, No. 2, pp. 127-140.
PCT/EP2009/055944 ISRWO Dated May 15, 2009.
Kosel, et.al. Diminished Gabaa Receptor-Binding Capacity and a DNA Base Substitution in a Patient With Treatment-Resistant Depression and Anxiety, Neuropsychopharmacology 2004, vol. 29, pp. 347-350.
GB0808832.0 Search Report Dated Sep. 12, 2008.

* cited by examiner

*Primary Examiner* — Jim Ketter (57) ABSTRACT

Differential expression of nucleic acids in the brains of subjects suffering from late-onset depression has been demonstrated. The invention provides methods useful in the determination of late-onset depression. Also provided by the present invention is a screening method for the identification of compounds for treatment, prevention or diagnosis of late-onset depression.

6 Claims, 2 Drawing Sheets

Figure 1: Coronal sections through the adult human forebrain at the anterior limit of the corpus callosum. Boxed areas (in black) mark out the subgenual anterior cingulate cortex.

Figure 2: Schematic coronal section through the adult human forebrain at the anterior limit of the striatum. Boxed area (in black) marks out the nucleus accumbens.

GABA BIOMARKERS FOR DEPRESSION

This application is a filing under 35 U.S.C. 371 of international application number PCT/EP2009/055944, filed May 15, 2009, which claims priority to Great Britain application number 0808832.0 filed May 15, 2008, the entire disclosure of which is hereby incorporated by reference.

TECHNICAL FIELD OF THE INVENTION

Biomarkers have been identified that are either upregulated or downregulated in brain tissue samples from subjects suffering from late-onset depression in comparison to brain tissue samples from non-depressed subjects. A screening method is provided by the present invention to identify compounds useful in the treatment, prevention, and diagnosis of late-onset depression. The present invention also provides methods that are useful in the treatment, prevention and diagnosis of late-onset depression.

DESCRIPTION OF RELATED ART

Depression affects 15% of the USA population at some point during their lives, and 100 million people are affected on any given day. The age of onset is fairly evenly spread and can come on suddenly in days or build over years. Over half of people who experience major depression have only one episode. However, with each successive episode, there is a 15% risk that the next episode will be a manic one, changing diagnosis to Bipolar Disorder. Ultimately, approximately 15-20% of those with major depression become chronically depressed and around 15% of patients with major depression may commit suicide; and men commit suicide twice as often as women.

At the current time, there is a limited understanding of the neurobiology involved in depression but it is becoming increasingly evident that this disease is multifaceted and may involve a myriad of elements that act either synergistically or independently to result in mood changes. Depression is a complex disorder and is not dominated by a single pathology that can be used as a marker for the purposes of treatment, diagnosis and screening. A number of neurotransmitter systems are involved, and several targets have been extensively studied, and have resulted in a range of treatment options. Treatments that are currently available include monoamine oxidase inhibitors (MAOIs), tricyclic antidepressants (TCAs), specific serotonin reuptake inhibitors (SSRIs), noradrenergic reuptake inhibitors (NRIs), serotonin noradrenergic reuptake inhibitors (SNRIs) and noradrenaline dopamine reuptake inhibitors (NDRIs). However, current anti-depressive drugs are unsatisfactory as they have many side effects, and have varying efficacy depending on the patient history and exact condition to be treated.

The gamma-aminobutyric acid (GABA) receptors are a class of receptors that respond to the neurotransmitter GABA, the chief inhibitory neurotransmitter in the vertebrate central nervous system. GABA receptors are reviewed by Bormann (2000 Trends Pharm. Sci.; 1(1): 16-19). There are three classes of GABA receptors: $GABA_A$, $GABA_B$, and $GABA_C$. $GABA_A$ and $GABA_C$ receptors are ionotropic receptors (also known as ligand-gated ion channels), whereas $GABA_B$ receptors are metabotropic receptors (also known as G protein-coupled receptors). The $GABA_A$ receptor directly gates a $Cl^-$ ionophore and has modulatory binding sites for benzodiazepines, barbiturates, neurosteroids and ethanol. $GABA_C$ receptors are $Cl^-$ pores that are insensitive to the drugs bicuculline and baclofen. By contrast, $GABA_B$ receptors couple to $Ca^{2+}$ and $K^+$ channels via G proteins and second messenger systems; they are activated by the agonist baclofen and are resistant to drugs that modulate $GABA_A$ receptors.

GABA receptors have been linked to mood disorders, including depression.

Emrich et al (Archiv Psychiatrie Nervenkrankheiten 1980; 229: 1-16) demonstrated efficacy of valproate in the treatment of manic depressive patients. They proposed that valproate, through the enhancement of GABA brain concentration, might compensate for a potential GABAergic deficiency. After Emrich's hypothesis, several animal and human studies evaluated the potential role of GABAergic abnormalities in the pathophysiology of depression (Krystal et al 2002 Mol. Psychiatry; 2: S71-S80; Merali et al 2004 J. Neurosci.; 24(6): 1478-1485; Bipolar Disorders, Basic Mechanisms and Therapeutic Implication. Marcel Dekker: New York, 2000, pp. 143-165). As reviewed by Brambilla et al (2003 Molecular Psychiatry; 8: 721-737), animal and clinical studies have suggested that a deficit in GABAergic activity may be involved in the pathophysiology of depression.

US 2005/0209181 discloses the expression profiles of human post-mortem brains from patients diagnosed with schizophrenia and suggests that the markers identified may also be useful in targeting depression. Amongst other targets, this patent publication suggests a link with depression for various subunits of the $GABA_A$ receptor, i.e. alpha 1, alpha 2, alpha 4, alpha 5, alpha 6, beta 1, gamma 2, delta.

In WO 2008/020435, altered expression was found in animal models of depression for various subunits of the $GABA_A$ receptor, i.e. alpha 1, alpha 2, alpha 3, alpha 4, alpha 5, alpha 6, beta 1, beta 2, delta, rho 3, theta. Altered expression was also found for the $GABA_B$ receptor.

In WO 02/20492 tetrahydroindazole derivatives are taught as being useful in the diagnosis and treatment of, amongst other diseases, depression. WO 02/20492 teaches that tetrahydroindazole derivatives act as agonists at alpha 2 or alpha 3 and as such are useful in the treatment of depressive or bipolar disorders.

However, these reported abnormalities may not be specific to depression, as GABAergic alterations have also been suggested in related pathologies, such as anxiety disorder (Kosel et al 2004 Neurophsychopharmacol; 29: 347-50) schizophrenia (Int J Neuropsychopharmacol 2002; 5: 159-179) and panic disorder (Biol Psychiatry 2000; 47: 96-106). Furthermore, in a study by Kugaya et al (2003 Biol Psychiatry; 54: 792-9) looking at the binding of the $GABA_A$ binding $[^{123}I]$ iomazenil in depressed patients, no difference was noted in depressed subjects in comparison to non-depressed subjects.

The neurobiological basis of late-onset depression remains largely unexplored, hampering the development of effective treatments. In the elderly, depression is the second most common psychiatric disorder after dementia, affecting approximately 3% of the over 65's, with a further 12% suffering milder yet still debilitating depression (Beekman et al *British Journal of Psychiatry* 174, 307-311 (1999)). Approximately one third of patients do not respond to initial anti-depressant therapy, while those who do respond remain at very high risk of relapse, chronicity and dementia (Cole et al *American Journal of Psychiatry* 156, 1182-1189 (1999)). Consequently late-onset depression is associated with considerable costs in terms of morbidity and mortality as well as health and social care burden. It has been suggested that the clinical management of late-onset depression should be more tailored to its specific pathophysiological profile as compared with depression in younger subjects (Thomas et al *American Journal of Psychiatry* 157, 1682-1684 (2000); Thomas et al *British Journal of Psychiatry* 181, 129-134 (2002)).

There is therefore a need for clinical strategies having particular application in the treatment and diagnosis of late-onset depression.

SUMMARY OF THE INVENTION

Differential expression of genes related to the GABA system has presently been demonstrated in the brains of subjects suffering from late-onset depression as compared to non-depressed subjects. A screening method is provided for the identification of compounds useful in the treatment, prevention or diagnosis of late-onset depression. Also provided are methods useful in the treatment, prevention and diagnosis of late-onset depression. The present invention has the advantage that it provides biomarkers that are specifically related to the pathophysiology of late-onset depression.

DETAILED DESCRIPTION OF THE INVENTION

In Vivo Imaging Method

The present invention provides an in vivo imaging method for use in the determination of whether a subject has or is predisposed to late-onset depression, said method comprising the steps of:

(i) administering an in vivo imaging agent to said subject, wherein said in vivo imaging agent comprises a compound that selectively associates with a polynucleotide or polypeptide, said polynucleotide or polypeptide being encoded by a GABAergic receptor gene, and wherein said compound is labelled with an in vivo imaging moiety;

(ii) allowing said in vivo imaging agent to selectively associate with said polynucleotide and/or said polypeptide expressed in a tissue of said subject;

(iii) detecting by an in vivo imaging method signals emitted by said in vivo imaging moiety; and, (iv) generating an image representative of the location and/or amount of said signals.

The term "in vivo imaging" as used herein refers to non-invasive techniques that produce images of all or part of the internal aspect of a subject following administration of an in vivo imaging agent.

The "subject" of the invention is preferably a mammal, most preferably an intact mammalian body in vivo. In an especially preferred embodiment, the subject is a human, and in particular a human suspected to have or to be predisposed to late-onset depression. The term "predisposed to" refers to a subject's susceptibility to develop a disease state based purely on genetic factors; in common parlance "nature" as opposed to "nurture".

"Late-onset depression" refers to major depressive disorder which first emerges in people aged 60 and over. The term "major depressive disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex, decreased energy, fatigue, being "slowed down", difficulty concentrating, remembering, or making decisions, insomnia, early-morning awakening, or oversleeping, appetite and/or weight loss or overeating and weight gain, thoughts of death or suicide or suicide attempts, restlessness or irritability, or persistent physical symptoms that do not respond to treatment, such as headaches, digestive disorders, and chronic pain.

"Administering" the in vivo imaging agent is preferably carried out parenterally, and most preferably intravenously. The intravenous route represents the most efficient way to deliver the in vivo imaging agent throughout the body of said subject. The in vivo imaging agent of the invention is preferably administered as a pharmaceutical composition which comprises the in vivo imaging agent along with a biocompatible carrier. The "biocompatible carrier" is a fluid, especially a liquid, in which the in vivo imaging agent is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

The "compound" comprised in the in vivo imaging agent may be a biomolecule, a small molecule, an aptamer, an antisense mRNA a small interference RNA, or an antibody. The term "biomolecule" includes molecules such as, e.g., lipids, nucleotides, polynucleotides, amino acids, peptides, polypeptides, proteins, carbohydrates and inorganic molecules. The term "small molecule" refers to an organic compound having a molecular weight of between 100 and 1000 Daltons. The term "antibody" refers to a protein produced by cells of the immune system or to a fragment thereof that binds to an antigen. The term "antisense mRNA" refers an RNA molecule complementary to the strand normally processed into mRNA and translated, or complementary to a region thereof. The term "aptamer" refers to an artificial nucleic acid binder (see, e.g., Ellington and Szostak (1990) Nature 346: 818-822). The term "small interference RNA" refers to a double-stranded RNA inducing sequence-specific posttranscriptional gene silencing (see, e.g., Elbashir et al. (2001) Genes Dev. 15:188-200). Preferably, the compound comprised in the in vivo imaging agent is a small molecule or a biomolecule, most preferably a small molecule. Particular features of an in vivo imaging agent suitable for imaging brain tissue are discussed in more detail below.

The term "selectively associates" refers to binding of the in vivo imaging agent to the target of interest, i.e. the polynucleotide or polypeptide encoded by a GABAergic receptor gene in preference to other tissues in order to facilitate discrimination of target tissue from non-target tissue by the method of the invention. Binding of the in vivo imaging agent to the target of interest may be determined using binding assays such as those described below in relation to the screening method of the invention.

The term "polynucleotide" refers to deoxyribonucleotides or ribonucleotides and polymers thereof in either single- or double-stranded form. A particular nucleic acid sequence also implicitly encompasses conservatively modified variants thereof e.g., degenerate codon substitutions, alleles, orthologs, single-nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term "nucleic acid" may be used to refer to a gene, complementary deoxyribonucleic acid (cDNA), and messenger ribonucleic acid (mRNA) encoded by a gene.

The term "polypeptide" refers to a polymer of amino acid residues. The term applies to amino acid polymers in which one or more amino acid residue is an artificial chemical mimetic of a corresponding naturally occurring amino acid, as well as to naturally occurring amino acid polymers and non-naturally occurring amino acid polymers. As used herein, the term encompasses amino acid chains of any length, including full-length proteins, wherein the amino acid residues are linked by covalent peptide bonds. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an alpha-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acids may be referred to herein by either the commonly known three letter symbols or by the one-letter symbols recommended by the IUPAC-IUB Biochemical Nomenclature Commission.

Where a polynucleotide is "encoded by" a gene, this means that the gene comprises the information required to (i) obtain complementary strands of deoxyribonucleic acid (DNA) by replication, or (ii) obtain mRNA by transcription. cDNA reverse transcribed from mRNA is also encompassed. Where a polypeptide is "encoded by" a gene, this means that the gene comprises the information required to (i) obtain mRNA by transcription, and (ii) obtain said polypeptide from said mRNA by translation. The terms "replication", "transcription" and "translation" take their accepted meaning in the field of the invention. That is, replication is the process by which DNA is copied into DNA, transcription is the process by which DNA is copied into mRNA, and translation is when the information in mRNA is used as a template for the synthesis of proteins.

A "GABAergic receptor" is a receptor that binds gamma-aminobutyric acid (GABA). A "GABAergic receptor gene" is therefore a gene encoding part of a GAGAergic receptor. Preferably, said GABAergic receptor gene is a gene encoding: $GABA_A$ receptor subunit $\alpha_1$ (GABRA1); $GABA_A$ receptor subunit $\alpha_4$ (GABRA4); $GABA_A$ receptor subunit $\alpha_5$ (GABRA5); $GABA_A$ receptor subunit $\beta_3$ (GABRB3); $GABA_A$ receptor subunit $\gamma_1$ (GABRG1), $GABA_A$ receptor subunit $\gamma_2$ (GABRG2); $GABA_A$ receptor subunit $\rho_1$ (GABRR1); $GABA_A$ receptor subunit $\delta$ (GABRD); $GABA_B$ receptor 2 (GABBR2); or, glycine receptor $\beta$ (GLRB).

The term "gene" means a segment of DNA involved in producing a polypeptide chain; it includes regions preceding and following the coding region (leader and trailer) as well as intervening sequences (introns) between individual coding segments (exons). With only a few exceptions, every cell of the body contains a full set of chromosomes and identical genes. Only a fraction of these genes are turned on, however, and it is the subset that is "expressed" that confers unique properties to each cell type. "Gene expression" is the term used to describe the transcription of the information contained within the DNA, the repository of genetic information, into messenger RNA (mRNA) molecules that are then translated into the proteins that perform most of the critical functions of cells. The kinds and amounts of mRNA produced by a cell are a reflection of which genes are expressed, which in turn provides insights into how the cell responds to its changing needs. Gene expression is a highly complex and tightly regulated process that allows a cell to respond dynamically both to environmental stimuli and to its own changing needs. This mechanism acts as both an on/off switch to control which genes are expressed in a cell as well as a volume control that increases or decreases the level of expression of particular genes as necessary.

The "in vivo imaging moiety" is any material that is detectable external to said subject's body following its administration to said subject. The presence of the in vivo imaging moiety provides a measure indicative of the amount of polypeptide or polynucleotide in the tissue being imaged. The term "labelled with an in vivo imaging moiety" means that the in vivo imaging moiety can be a constitutive part of the compound, or may be a separate entity conjugated to the compound. Where the in vivo imaging moiety is conjugated to the compound, an optional linker moiety links the vector and the in vivo imaging moiety together.

Following the administering step and preceding the detecting step, the in vivo imaging agent is allowed to selectively associate with said polynucleotide and/or said polypeptide. For example, when the subject is an intact mammal, the in vivo imaging agent will dynamically move through the mammal's body, coming into contact with various tissues therein. Once the in vivo imaging agent comes into contact with a tissue expressing said polynucleotide and/or said polypeptide, a specific interaction takes place such that clearance of the in vivo imaging agent from said tissue takes longer than from other tissues, thereby enabling an image representative of specifically associated in vivo imaging agent to be generated.

The term "tissue" is used to describe a collection of cells associated together to perform a particular biological function. The fundamental types of tissues in subjects of the present invention are epithelial, nerve, connective, muscle, and vascular tissues. A preferred tissue in the context of the in vivo imaging method of the present invention is brain tissue.

The step of "detecting" the level of the in vivo imaging agent selectively associated with said polynucleotide or a polypeptide in said subject is enabled by the presence of said in vivo imaging moiety. A suitable in vivo imaging technique is one that can detect signals emitted by said in vivo imaging moiety and generate data which is indicative of the location and/or amount of in vivo imaging moiety present in said tissue of said subject. For example, SPECT can be used as the detection technique where the in vivo imaging moiety emits gamma rays.

Preferred brain tissues in the context of the in vivo imaging method of the present invention are located in the anterior cingulate and in the nuclear accumbens. Both of these regions of the brain are implicated in the clinical symptoms of depression and are demonstrated herein to be associated with altered expression of GABAergic genes in late-onset depression. Where the brain tissue being imaged is in the anterior cingulate, a preferred GABAergic receptor gene is a gene encoding GABBR2, GABRG1, or GABRR1, most preferably a gene encoding GABBR2 or GABRR1. Where the brain tissue being imaged is in the nucleus accumbens, a preferred GABAergic receptor gene is a gene encoding GABRA4, GABRB3, or GABRG2, most preferably a gene encoding GABRB3.

Particular requirements apply for an in vivo imaging agent to be suitable for imaging brain tissue. In the brain, endothelial cells are packed together more tightly than in the rest of the body by means of "tight junctions", which are multifunctional complexes that form a seal between adjacent epithelial cells, preventing the passage of most dissolved molecules from one side of the epithelial sheet to the other. This so-called blood-brain barrier (BBB) blocks the movement of all molecules except those that cross cell membranes by means of lipid solubility (such as oxygen, carbon dioxide, ethanol, and steroid hormones) and those that are allowed in by specific transport systems (such as sugars and some amino acids). Substances with a molecular weight higher than 500 Daltons generally cannot cross the BBB by passive diffusion, while smaller molecules often can. In addition to tight junctions acting to prevent transport in between endothelial cells, there are two mechanisms to prevent passive diffusion. Glial cells surrounding capillaries in the brain pose a secondary hindrance to hydrophilic molecules, and the low concentration of interstitial proteins in the brain also prevents access by hydrophilic molecules.

Lipid solubility is commonly assessed by measuring the octanol-water partition coefficient (P), typically expressed as a $\log_{10}$ value, referred to herein as "logP". The octanol-water partition coefficient represents the distribution of a substance between an organic and aqueous phase. The logP provides a simple way of determining the lipophilicity or hydrophilicity of a compound.

The ratio is defined as;

Partition=[compound present in octanol]/[compound present in water]

This equation can be expressed as:

Log Partition=$\log_{10}$ [compound present in octanol]/[compound present in water]

In simple terms the greater the positive number of the logP calculation the greater the lipophilicity of the compound. Calculation of the logP is typically determined for potential new pharmaceutical compounds as it provides an insight into how the compound will be compartmentalised within the body following administration.

The logP of an in vivo imaging agent suitable for use in the present invention is in the range 1.0-4.5, preferably in the range 1.0-3.5, and most preferably in the range 2.0-3.5. An estimated logP value (AlogP98) can be obtained prior to evaluation in vitro and in vivo, e.g. using DS MedChem Explorer software (Accelerys). In addition to being advantageous for CNS penetration, lipophilicity in this range permits rapid clearance for in vivo imaging, which is particularly important when the radioactive halogen is a relatively short-lived radioisotope, such as $^{18}$F.

The BBB penetration properties of a particular in vivo imaging agent may be estimated in silico by comparison with literature in vivo brain penetration data using Accelerys DS MedChem Explorer software. The "logBbR" is the $\log_{10}$ of [brain concentration]/[blood concentration]. The logBbR for in vivo imaging agents used in the method of the present invention is suitably in the range 0.0-1.0, preferably in the range 0.3 to 1.0, most preferably in the range 0.5-0.7.

A preferred in vivo imaging moiety for use in the in vivo imaging method of the invention is chosen from:
  a radioactive metal ion;
  (ii) a paramagnetic metal ion;
  (iii) a gamma-emitting radioactive halogen;
  (iv) a positron-emitting radioactive non-metal; and,
  (v) a hyperpolarised NMR-active nucleus.

When the in vivo imaging moiety is a radioactive metal ion, i.e. a radiometal, suitable radiometals can be either positron emitters such as $^{64}$Cu, $^{48}$V, $^{52}$Fe, $^{55}$Co, $^{94m}$Tc or $^{68}$Ga; or γ-emitters such as $^{99m}$Tc, $^{111}$In, $^{113m}$In, or $^{67}$Ga. Preferred radiometals are $^{99m}$Tc, $^{64}$Cu, $^{68}$Ga and $^{111}$In. Most preferred radiometals are γ-emitters, especially $^{99m}$Tc.

When the in vivo imaging moiety is a paramagnetic metal ion, suitable such metal ions include: Gd(III), Mn(II), Cu(II), Cr(III), Fe(III), Co(II), Er(II), Ni(II), Eu(III) or Dy(III). Preferred paramagnetic metal ions are Gd(III), Mn(II) and Fe(III), with Gd(III) being especially preferred.

When the in vivo imaging moiety is a gamma-emitting radioactive halogen, the radiohalogen is suitably chosen from $^{123}$I, $^{131}$I or $^{77}$Br. $^{125}$I, while suitable for use as a detectable label in the in vitro screening method described herein, is not suitable for use as an in vivo imaging moiety. A preferred gamma-emitting radioactive halogen is $^{123}$I.

When the in vivo imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

When the in vivo imaging moiety is a hyperpolarised NMR-active nucleus, such NMR-active nuclei have a non-zero nuclear spin, and include $^{13}$C, $^{15}$N, $^{19}$F, $^{29}$Si and $^{31}$P. Of these, $^{13}$C is preferred. By the term "hyperpolarised" is meant enhancement of the degree of polarisation of the NMR-active nucleus over its equilibrium polarisation. The natural abundance of $^{13}$C (relative to $^{12}$C) is about 1%, and suitable $^{13}$C-labelled compounds are suitably enriched to an abundance of at least 5%, preferably at least 50%, most preferably at least 90% before being hyperpolarised. At least one carbon atom of the in vivo imaging agent of the invention is suitably enriched with $^{13}$C, which is subsequently hyperpolarised.

Preferred in vivo imaging moieties for the present invention are those which can be detected externally in a non-invasive manner following administration in vivo, such as by means of SPECT, PET and MRI. Most preferred in vivo imaging moieties for in vivo imaging are radioactive, especially radioactive metal ions, gamma-emitting radioactive halogens and positron-emitting radioactive non-metals, particularly those suitable for imaging using SPECT or PET.

Preferred in vivo imaging agents of the invention do not undergo facile metabolism in vivo, and hence most preferably exhibit a half-life in vivo of 60 to 240 minutes in humans. The in vivo imaging agent is preferably excreted via the kidney (i.e. exhibits urinary excretion). The in vivo imaging agent preferably exhibits a signal-to-background ratio at diseased foci of at least 1.5, most preferably at least 5, with at least 10 being especially preferred. Where the in vivo imaging agent comprises a radioisotope, clearance of one half of the peak level of in vivo imaging agent which is either non-specifically bound or free in vivo, preferably occurs over a time period less than or equal to the radioactive decay half-life of the radioisotope of the in vivo imaging moiety.

Furthermore, the molecular weight of the in vivo imaging agent is suitably up to 5000 Daltons. Preferably, the molecular weight is in the range 100 to 3000 Daltons, most preferably 200 to 1000 Daltons. Furthermore, and as mentioned above, for an in vivo imaging agent to be suitable for imaging brain tissue, it is desirable for the in vivo imaging agent to have a molecular weight of less than 500 Daltons. An especially preferred molecular weight for the in vivo imaging agent is therefore in the range 200-500 Daltons.

Where the in vivo imaging agent comprises a polypeptide and an in vivo imaging moiety, the in vivo imaging moiety is conjugated via either the polypeptide's N- or C-terminus, or via any of the amino acid side chains. Preferably, the in vivo imaging moiety is conjugated to the polypeptide via either the N- or C-terminus, optionally via a linker such as a polyethylene glycol linker.

Alternatively, functional group of the in vivo imaging agent may comprise the in vivo imaging moiety. When a functional group comprises an in vivo imaging moiety, this means that the in vivo imaging moiety forms part of the chemical structure of the in vivo imaging agent. For example, the in vivo imaging moiety may be a radioactive isotope present at a level significantly above the natural abundance level of said isotope. Such elevated or enriched levels of isotope are suitably at least 5 times, preferably at least 10 times, most preferably at least 20 times; and ideally either at least 50 times the natural abundance level of the isotope in question, or present at a level where the level of enrichment of the isotope in question is 90 to 100%. Examples of such functional groups include iodophenyl groups with elevated levels of $^{123}$I, $CH_3$ groups with elevated levels of $^{11}$C, and fluoroalkyl groups with elevated levels of $^{18}$F, such that the imaging moiety is the isotopically labelled $^{11}$C or $^{18}$F atom within the chemical structure.

A compound that selectively associates with a polynucleotide or a polypeptide encoded by a GABAergic receptor gene may be identified and obtained using the screening method of the invention, which is described in more detail below. Where said screening method is a binding assay, it is desirable that the compound binds to the target of interest with nanomolar potency, i.e. having a dissociation constant ($K_d$) of between 0.01-100 nM, preferably between 0.01-10 nM and most preferably between 0.01-1.0 nM. Labelling of such a compound to provide an in vivo imaging agent may conveniently be carried out by reaction of a precursor compound with a suitable source of the desired in vivo imaging moiety. A "precursor compound" comprises an unlabelled derivative of the imaging agent, designed so that chemical reaction with a convenient chemical form of the in vivo imaging moiety occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity. The precursor compound may optionally comprise a protecting group for certain functional groups of the precursor compound.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection, the desired in vivo imaging agent is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene) ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

When the in vivo imaging moiety is a metal ion, such as $^{99m}$Tc for SPECT or Gd(III) for MRI, the in vivo imaging agent preferably comprises a metal complex of the radioactive metal ion with a synthetic ligand. By the term "metal complex" is meant a coordination complex of the metal ion with one or more ligands. It is strongly preferred that the metal complex is "resistant to transchelation", i.e. does not readily undergo ligand exchange with other potentially competing ligands for the metal coordination sites. Potentially competing ligands include other excipients in the preparation in vitro (e.g. radioprotectants or antimicrobial preservatives used in the preparation), or endogenous compounds in vivo (e.g. glutathione, transferrin or plasma proteins). The term "synthetic" has its conventional meaning, i.e. man-made as opposed to being isolated from natural sources e.g. from the mammalian body. Such compounds have the advantage that their manufacture and impurity profile can be fully controlled.

Suitable ligands for use in the present invention which form metal complexes resistant to transchelation include: chelating agents, where 2-6, preferably 2-4, metal donor atoms are arranged such that 5- or 6-membered chelate rings result (by having a non-coordinating backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes, and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as MIBI (i.e. 1-isocyano-2-methoxy-2-methylpropane). Examples of suitable phosphines include Tetrofosmin, and monodentate phosphines such as tris(3-methoxypropyl) phosphine. Examples of suitable diazenides include the HYNIC series of ligands i.e. hydrazine-substituted pyridines or nicotinamides.

The above described ligands are particularly suitable for complexing technetium e.g. $^{94m}$Tc or $^{99m}$Tc, and are described more fully by Jurisson et al [Chem. Rev., 99, 2205-2218 (1999)]. The ligands are also useful for other metals, such as copper ($^{64}$Cu or $^{67}$Cu), vanadium (e.g. $^{48}$V) iron (e.g. $^{52}$Fe), or cobalt (e.g. $^{55}$Co).

Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. Particularly preferred for gadolinium are chelates including DTPA, ethylene diamine tetraacetic acid (EDTA), triethylene tetraamine hexaacetic acid (TTHA), 1,4,7,10-tetraazacyclododecane-1,4,7,10-tetraacetic acid (DOTA), 10-(2-hydroxypropyl)-1,4,7,10-tetraazacyclododecane-1,4,7-triacetic acid (DO3A) and derivatives of these.

Where the in vivo imaging moiety is radiohalogen, preferred precursor compounds are those which comprise a derivative which either undergoes electrophilic or nucleophilic radiohalogenation or undergoes condensation with a labelled aldehyde or ketone. Examples of the first category are:

(a) organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates);

(b) a non-radioactive alkyl bromide for halogen exchange or alkyl tosylate, mesylate or triflate for nucleophilic iodination;

(c) aromatic rings activated towards nucleophilic iodination (e.g. aryl iodonium salt aryl diazonium, aryl trialkylammonium salts or nitroaryl derivatives).

The precursor preferably comprises: a non-radioactive halogen atom such as an aryl iodide or bromide (to permit radiohalogen exchange); an organometallic precursor compound (e.g. trialkyltin, trialkylsilyl or organoboron compound); or an organic precursor such as triazenes or a good leaving group for nucleophilic substitution such as an iodonium salt. Preferably for radioiodination, the precursor comprises an organometallic precursor compound, most preferably trialkyltin.

Precursors and methods of introducing radioiodine into organic molecules are described by Bolton [J. Lab. Comp. Radiopharm., 45, 485-528 (2002)]. Suitable boronate ester organoboron compounds and their preparation are described by Kabalka et al [Nucl. Med. Biol., 29, 841-843 (2002) and 30, 369-373 (2003)]. Suitable organotrifluoroborates and their preparation are described by Kabalka et al [Nucl. Med. Biol., 31, 935-938 (2004)].

Radiofluorination may be carried out via direct labelling using the reaction of $^{18}$F-fluoride with a suitable chemical group in the precursor having a good leaving group, such as an alkyl bromide, alkyl mesylate or alkyl tosylate. $^{18}$F can also be introduced by alkylation of N-haloacetyl groups with a $^{18}$F(CH$_2$)$_3$OH reactant, to give —NH(CO)CH$_2$O(CH$_2$)$_3$$^{18}$F derivatives. For aryl systems, $^{18}$F-fluoride nucleophilic displacement from an aryl diazonium salt, aryl nitro compound or an aryl quaternary ammonium salt are suitable routes to aryl-$^{18}$F derivatives.

A $^{18}$F-labelled in vivo imaging agent may be obtained by formation of $^{18}$F fluorodialkylamines and subsequent amide formation when the $^{18}$F fluorodialkylamine is reacted with a precursor containing, e.g. chlorine, P(O)Ph$_3$ or an activated ester. Further approaches for radiofluorination, particularly suitable for radiofluorination of peptides, are described in WO 03/080544, which uses thiol coupling, and in WO 04/080492, which makes use of aminoxy coupling. Further details of synthetic routes to $^{18}$F-labelled derivatives are described by Bolton, J. Lab. Comp. Radiopharm., 45, 485-528 (2002).

The in vivo imaging agent of the method of the invention may be easily obtained by means of a kit. Such kits comprise a suitable precursor compound, preferably in sterile non-pyrogenic form, so that reaction with a sterile source of an in vivo imaging moiety gives the desired in vivo imaging agent with the minimum number of manipulations. Such considerations are particularly important in the case of radioactive in vivo imaging agents, in particular where the radioisotope has a relatively short half-life, for ease of handling and hence reduced radiation dose for the radiopharmacist.

The reaction medium for reconstitution of such kits is preferably a biocompatible carrier, as defined previously herein, such that a pharmaceutical composition comprising said in vivo imaging agent is obtained.

In the in vivo imaging method of the invention, the detecting step is followed by a step of generating an image representative of the signals emitted by the in vivo imaging moiety. This generating step of the method of the invention is carried out by a computer which applies a reconstruction algorithm to the acquired signal data to yield a dataset. This dataset is then manipulated to generate images showing areas of interest within the subject. These images provide information that is useful in a method for the diagnosis of late-onset depression.

Method of Diagnosis

In another aspect, the present invention provides an in vivo imaging agent as defined above in relation to the in vivo imaging method for use in a method for the diagnosis of late-onset depression.

Furthermore, the present invention provides a method for the diagnosis of late-onset depression comprising:

(a) the in vivo imaging method as defined above; and,
(b) comparing the image generated in step (a) with an in vivo image representative of the pattern of uptake of said in vivo imaging agent when said in vivo imaging method is carried out in non-depressed subjects.

The suitable and preferred embodiments of the tissue and subject of the method of diagnosis are as defined for the method of in vivo imaging above.

Variation of levels of a polypeptide or polynucleotide described herein from the image representative of a non-depressed subject (either up or down) indicates that the subject has late-onset depression or is at risk of developing at least some aspects of late-onset depression.

The image representative of uptake of said in vivo imaging agent when said in vivo imaging method is carried out in non-depressed subjects is obtained by carrying out the in vivo imaging method as defined above on a suitably-matched cohort of non-depressed subjects, and producing an image which represents an average of all the images obtained.

Method for Treatment

Compounds that modulate the activity of a GABAergic receptor can be administered to a subject for the treatment of late-onset depression. The present invention therefore provides a method for treatment of a subject suffering from late-onset depression, said method comprising administration of a pharmaceutical composition, said pharmaceutical composition comprising:

(a) a pharmaceutically effective amount of a compound that modulates the activity of a GABAergic receptor by selectively associating with a polynucleotide or polypeptide, said polynucleotide or polypeptide being encoded by a GABAergic receptor gene, said GABAergic receptor gene being a preferred GABAergic receptor gene as defined above in relation to the in vivo imaging method of the invention; and,
(b) a biocompatible carrier.

The biocompatible carrier is broadly as defined earlier in the specification. The particular biocompatible carrier selected is determined in part by the particular pharmaceutical composition being administered, as well as by the particular method used to administer the composition. Accordingly, there is a wide variety of suitable formulations of pharmaceutical compositions (see, e.g. *Remington's Pharmaceutical Sciences,* 17th ed. 1985)). Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives.

Administration for treatment is by any of the routes normally used for introducing a pharmaceutical compound into contact with the tissue to be treated and is well known to those of skill in the art. Although more than one route can be used to administer a particular composition, a particular route can often provide a more immediate and more effective reaction than another route. In the practice of this invention, the pharmaceutical composition can be administered, for example, orally, nasally, topically, intravenously, intraperitoneally, or intrathecally. The pharmaceutical composition can be presented in unit-dose or multi-dose sealed containers, such as ampoules and vials. Solutions and suspensions can be prepared from sterile powders, granules, and tablets of the kind previously described. The pharmaceutical composition can also be administered as part of a prepared food or drug. A "pharmaceutically effective amount" of a compound is a dose sufficient to affect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the mental disorder. The size of the dose also will be determined by the existence, nature, and extent of any adverse side effects that accompany the administration of a particular pharmaceutical composition to a particular subject.

In determining the effective amount of the pharmaceutical composition to be administered, a physician may evaluate circulating plasma levels of the pharmaceutical composition, pharmaceutical composition toxicity, and the production of anti-pharmaceutical composition antibodies. In general, the dose equivalent of a compound is from about 1 ng/kg to 10 mg/kg for a typical subject. For administration, the pharmaceutical composition can be administered at a rate determined by the LD-50 of the compound, and the side effects of the compound at various concentrations, as applied to the mass and overall health of the subject.

The term "modulates the activity of a GABAergic receptor" means that the compound has an effect on said GABAergic receptor that acts to bring the activity of said receptor closer to that seen in non-depressed subjects.

Furthermore, the in vivo imaging agent as defined above in relation to the in vivo imaging method of the invention can be applied for use in a method to decide whether to implement the method for treatment as defined above, said method to decide comprising:
 (a) the in vivo imaging method as defined herein; and,
 (b) evaluating the image generated by the in vivo imaging method of step (a) to decide whether to implement said method for treatment.

Screening Method

In another aspect, the present invention provides a screening method to identify a compound that selectively associates with a polynucleotide or a polypeptide, said method comprising:
 (i) contacting said compound with a polypeptide or a polynucleotide, said polynucleotide or polypeptide being encoded by a GABAergic receptor gene; and,
 (ii) determining the effect of said compound upon said polypeptide or said polynucleotide;
wherein said GABAergic receptor gene is a gene as defined above for the in vivo imaging method of the invention, preferably a gene encoding a GABAergic receptor selected from: $GABA_A$ receptor subunit $\alpha_1$ (GABRA1); $GABA_A$ receptor subunit $\alpha_4$ (GABRA4); $GABA_A$ receptor subunit $\alpha_5$ (GABRA5); $GABA_A$ receptor subunit $\beta_3$ (GABRB3); $GABA_A$ receptor subunit $\gamma_1$ (GABRG1), $GABA_A$ receptor subunit $\gamma_2$ (GABRG2); $GABA_A$ receptor subunit $\rho_1$ (GABRR1); $GABA_A$ receptor subunit $\delta$ (GABRD); $GABA_B$ receptor 2 (GABBR2); or, glycine receptor $\beta$ (GLRB).

A "compound" useful in the treatment, prevention or diagnosis of late-onset depression may be a biomolecule, a small molecule, an aptamer, an antisense mRNA a small interference RNA, or an antibody. The terms "biomolecule", "small molecule", "antibody", "antisense mRNA", "aptamer", "small interference RNA" take the meanings provided earlier in the specification.

In its broadest sense, the step of "contacting" said compound with a polypeptide or a polynucleotide means bringing said compound and said polypeptide or polynucleotide into physical contact with each other. This may be accomplished either in vitro or in vivo, as described in further detail below.

The "effect of the compound" is any specific interaction between the compound and the polynucleotide or the polypeptide. Such specific interaction encompasses specific binding of the compound with the polynucleotide or the polypeptide, and includes any modulation of the level of expression or activity of the polynucleotide or polypeptide induced by the compound.

The step of "determining" the effect of the compound can be carried out by methods well-known in the art. An example of such a well-known screening method is one where the effect determined in the determining step is binding of said compound to said polypeptide or polynucleotide. Such binding assays preferably involve contacting an isolated polypeptide or polynucleotide described herein with one or more compounds and allowing sufficient time for the polypeptide or polynucleotide and compound to form a binding complex. The term "isolated" means separated from other cell components, and may also include synthetic polynucleotides and polypeptides. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g. Bennet and Yamamura, (1985) "Neurotransmitter, Hormone or Drug Receptor Binding Methods" in *Neurotransmitter Receptor Binding* (Yamamura, H. I., et al., eds., pp. 61-89). The protein utilized in such assays can be naturally expressed, cloned or synthesized. Binding assays are also useful, e.g., for identifying endogenous proteins that interact with a polypeptide. For example, antibodies, receptors or other molecules that bind a polypeptide can be identified in binding assays. In many cases, at least one of the reactants in the binding assay comprises a detectable label. The term "reactants" in this context including the compound, the polypeptide, the polynucleotide, or any antibodies used to specifically detect them. The "detectable label" can be any material having a detectable physical or chemical property. The presence of detectable label therefore provides a measure indicative of the amount of bound reactant. Depending on the particular detectable label used, a suitable detection technique is used to measure the amount of selectively-bound detectable label. Detectable labels suitable for use in the screening method of the invention include those detectable in vitro by spectroscopic, photochemical, biochemical, immunochemical, electrical, optical or chemical means including:
  (i) magnetic beads (e.g., Dynabeads™);
  (ii) fluorescent dyes (e.g., fluorescein isothiocyanate, Texas red, rhodamine, and the like);
  (iii) radiolabels (e.g., $^3$H, $^{125}$H, $^{35}$S, $^{14}$C, or $^{32}$P);
  (iv) enzymes (e.g., horse radish peroxidase, alkaline phosphatase and others commonly used in an ELISA); and,
  (v) calorimetric labels such as colloidal gold or coloured glass or plastic (e.g., polystyrene, polypropylene, latex, etc.) beads.

Means of detecting these detectable labels are well known to those of skill in the art. Thus, for example, where the detectable label is a radioactive label, means for detection include a scintillation counter or photographic film as in autoradiography. Where the detectable label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CODs) or photomultipliers and the like. Similarly, enzymatic detectable labels may be detected by providing the appropriate substrates for the enzyme and detecting the resulting reaction product.

The screening method of the present invention may also preferably be carried out in vitro wherein said polypeptide or polynucleotide is expressed in a cell and the cell is contacted with the compound. Such methods generally involve conducting cell-based assays in which compounds are contacted with one or more cells expressing a polypeptide or polynucleotide described herein, and then detecting an increase or decrease in expression of transcript, translation product, or catalytic product. The expression level of a polynucleotide described herein in a cell can be determined by measuring the mRNA expressed in a cell with a compound that specifically hybridizes with a transcript (or complementary nucleic acid) of said polynucleotide. Measurement can be conducted by lysing the cells and conducting Northern blots or without lysing the cells using in situ hybridization techniques.

A polypeptide can be detected using immunological methods in which a cell lysate is probed with compounds that are antibodies which specifically bind to said polypeptide.

Catalytic activity of polypeptides can be determined by measuring the production of enzymatic products or by measuring the consumption of substrates. Activity refers to either the rate of catalysis or the ability to the polypeptide to bind ($K_m$) the substrate or release the catalytic product ($K_d$).

Analysis of the activity of polypeptides can be performed according to general biochemical analyses. Such assays include cell-based assays as well as in vitro assays involving purified or partially purified polypeptides or crude cell lysates. The assays generally involve providing a known quantity of substrate and quantifying product as a function of time.

The screening method can also be carried out wherein said contacting step comprises administration of said compound to an animal model of late-onset depression. The animal models utilized generally are mammals of any kind. Specific examples of preferred animals include, but are not limited to, primates, mice, and rats. In one embodiment, rat models of depression (both chronic and acute), in which the rats are subjected to stress, are used for screening. In one embodiment, invertebrate models such as *Drosophila* models can be used, screening for modulators of *Drosophila* orthologs of the human genes disclosed herein. In another embodiment, transgenic animal technology including gene knockout technology, for example as a result of homologous recombination with an appropriate gene targeting vector, or gene overexpression, will result in the absence, decreased or increased expression of a polynucleotide or polypeptide. Transgenic animals generated by such methods find use as animal models of mental disorders and are useful in screening for modulators of mental disorders.

Knockout cells and transgenic mice can be made by insertion of a marker gene or other heterologous gene into an endogenous gene site in the mouse genome via homologous recombination. Such mice can also be made by substituting an endogenous polynucleotide with a mutated version of the polynucleotide, or by mutating an endogenous polynucleotide, e.g., by exposure to carcinogens.

In a preferred embodiment, the screening method as described in any of the above embodiments concerns contacting said compound with said polypeptide and determining the effect of said compound on said polypeptide.

Methods Used in the Present Invention

Studies are described herein that investigate the expression patterns of genes that are differentially expressed specifically in brain tissue of subjects with late-onset depression. The large spectrum of symptoms associated with depression reflects the complex genetic basis and complex gene expression patterns in these subjects. Furthermore, brain pathways or circuits as well as subcellular pathways are important for understanding the development and diagnosis of mental disorders. The selected brain regions evaluated (anterior cingulate (AC) and nucleus accumbens (NA)) are implicated in the clinical symptoms of depression.

Cytoarchitectual changes in brain regions, expression of key neurotransmitters or related molecules in brain regions, and subcellular pathways in brain regions all contribute to the development of depression.

The data on which the present invention is based was obtained by microarray expression analysis. The arrays used in this kind of analysis are called "expression chips". The immobilized DNA is cDNA reverse transcribed from the mRNA of known genes, and once again, at least in some experiments, the control and sample DNA hybridized to the chip is cDNA reverse transcribed from the mRNA of normal and diseased tissue, respectively. If a gene is overexpressed in a certain disease state, then more sample cDNA, as compared to control cDNA, will hybridize to the spot representing that expressed gene. In turn, the spot will fluoresce red with greater intensity than it will fluoresce green. Once researchers have characterized the expression patterns of various genes involved in many diseases, cDNA derived from diseased tissue from any individual can be hybridized to determine whether the expression pattern of the gene from the individual matches the expression pattern of a known disease. If this is the case, treatment appropriate for that disease can be initiated.

A useful review of microarray methodology can be found in Nature Genetics January 1999 supplement. Of most relevance for the present invention is the article by Botwell on pages 25-32, which describes how to obtain expression data using microarray technology. An overview of the technology is now provided.

DNA "microarrays" are small, solid supports onto which the sequences from thousands of different genes are immobilized, or attached, at fixed locations. The supports themselves are usually glass microscope slides, but can also be silicon chips or nylon membranes. The DNA is printed, spotted, or actually synthesized directly onto the support. It is important that the gene sequences in a microarray are attached to their support in an orderly or fixed way, because the location of each spot in the array is used to identify a particular gene sequence. The spots themselves can be DNA, cDNA, or oligonucleotides. Microarrays can be prepared by the researcher or sourced commercially, depending on issues of e.g. cost, timing, and human resource available. Genechip®arrays are commercially available arrays that are manufactured using technology that combines photolithography and combinatorial chemistry (www.affymetrix.com). Up to 1.3 million different oligonucleotide probes are synthesized on each array. Each oligonucleotide is located in a specific area on the array called a probe cell. Each probe cell contains hundreds of thousands to millions of copies of a given oligonucleotide.

To obtain cDNA from mRNA, reverse transcription is used, a process in which a DNA polymerase enzyme, known as a reverse transcriptase, transcribes single-stranded ribonucleic acid (RNA) into double-stranded DNA. Typically, a poly-T (thymidine) primer is used as the primer in this reaction as mRNA has a poly-A (adenosine) tail.

The quality of the input mRNA is crucial in order to obtain cDNA suitable for microarray analysis. RNA integrity in post-mortem sampling can be influenced by pre-mortem and post-mortem events, as well as by interrelations between expression level and confounding factors such as donor age of death, pre-mortem hypoxia, agonal events and duration of agonal stage, brain pH, post-mortem interval before sampling, and RNA integrity (Stan et al 2006; Brain Research; 1123(1): 1-11). It is therefore important to screen RNA samples to select those that will be suitable for microarray analysis. A simple pH measurement can be done on the sample as an indication of agonal state, prior to evaluation of the quality of the RNA. Thereafter, various methods can be used to measure RNA quality (Copois et al 2007 J Biotechnol; 127(4): 549-59), one of which is the RNA integrity number (RIN, Agilent Technologies). Using electrophoretic separation on microfabricated chips, RNA samples are separated and subsequently detected via laser induced fluorescence detection. The bioanalyzer software generates an electropherogram and gel-like image and displays results such as sample concentration and the so-called ribosomal ratio (the 18S to 28S ribosomal band ratio). Standardized interpretation of the RNA integrity data is carried out using the RIN software algorithm, which allows for the classification of riboeukaryotic total RNA, based on a numbering system from 1 to 10, with 1 being the most degraded profile and 10 being the most intact.

DNA microarray technology facilitates the identification and classification of DNA sequence information and the assignment of functions to these new genes. A microarray works by exploiting the ability of a given mRNA molecule to bind specifically to, or hybridize to, the DNA template from which it originated. The term "hybridize" refers to the process of combining, or annealing, complementary single-stranded nucleic acids into a single double-stranded molecule. By using an array containing many DNA samples it is possible to determine, in a single experiment, the expression levels of hundreds or thousands of genes within a cell by measuring the amount of mRNA bound to each site on the array. With the aid of a computer, the amount of mRNA bound to the spots on the microarray is precisely measured, generating a profile of gene expression in the cell.

An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). "Stringent" conditions will be those in which the salt concentration is less than about 1.0 M sodium ion, typically about 0.01 to 1.0 M sodium ion concentration (or other 10 salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

After the hybridization step is complete, the microarray is placed in a "reader" or "scanner" that consists of some lasers, a special microscope, and a camera. Examples include the Packard BioChip Imager, Molecular Dynamics Avalanche and Genetic Microsystems GMS 418 Array Scanner. The fluorescent tags are excited by the laser, and the microscope and camera work together to create a digital image of the array. A typical microarray experiment generates thousands of data points, which means that sophisticated techniques for storing and processing data are required. The tools that are used may comprise software to perform image analysis of data from readers, databases to store and link information, and software that links data from individual clones to web databases, such as GenBank. The GenBank sequence database is an open access, annotated collection of all publicly available nucleotide sequences and their protein translations (http://www.ncbi.nlm.nih.gov/sites/entrez?db=nucleotide). This database is produced at National Center for Biotechnology Information (NCBI) as part of the International Nucleotide Sequence Database Collaboration, or INSDC.

Microarrays were presently used to analyse the mRNA expression profile of samples taken from the post-mortem brains of subjects having late-onset depression. The anterior cingulate and nuclear accumbens were selected for analysis as these areas of the brain are known to be associated with the pathophysiology of depression. Altered expression of the genes related to the GABAergic system (Tables 2 and 4 in the Examples below) has been shown at the mRNA level in selected brain regions of patients diagnosed with depression in comparison with normal individuals. The specific protocols used to obtain the data on which the present invention is based are now described in detail.

Brief Description of the Examples

Example 1 describes the methods employed in carrying out transcriptomics analysis on anterior cingulate samples from depressed and non-depressed subjects.

Example 2 describes the methods employed in carrying out transcriptomics analysis on nuclear accumbens samples from depressed and non-depressed subjects.

EXAMPLES

Example 1

Anterior Cingulate Transcriptomics

Example 1(i) Sample Selection

Frozen brain tissue (stored at −80° C.) was obtained from the frontal cortex of 10 subjects with late-onset depression, and matched for age, sex, post mortem interval and agonal state with 10 psychiatrically healthy control subjects. All subjects died suddenly, with a mean duration of agonal state of about 7 hours (Li et al *Hum Mol Genet.* 13, 609-616 (2004)). These numbers were selected as being sufficient to detect group differences at conventional significance levels on the microarray of >±2SD, or using DIGE based proteomic analysis. Depressed subjects had all had DSM-IV major depression and case note review confirmed this and they had no other mental illness. Case notes for controls were screened to ensure they had not had any psychiatric disorder. All subjects received a postmortem and neuropathological examination and none had changes consistent with dementia.

The tissue was screened for its suitability for use by assessing pH as a marker of agonal state. Samples were obtained from storage at −80° C., subdissected, thawed and a 10% homogenate (e.g. 1 gram tissue plus 9 ml water) prepared by homogenising for 10 seconds at full speed with a UltraTurrax homogeniser. Sample pH was determined using a silver chloride electrode calibrated with aqueous standards.

Example 1(ii) Microarray Analysis

Figure 1:
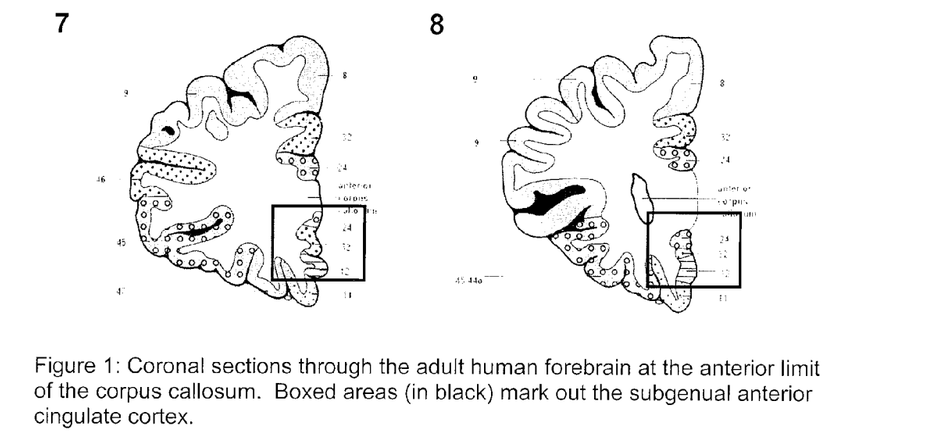
FIG. 1 shows coronal sections through the adult human forebrain at the anterior limit of the corpus callosum. Boxed areas (in black) mark out the subgenual anterior cingulate cortex.

Following evaluation, a restricted set of samples was available for analysis (see Table 1 below). From this sample set, subgenual anterior cingulate cortex (see FIG. 1) was selected and microdissected at −20° C. These samples were stored frozen at −80° C. and subsequently processed for RNA analysis. For preparation of RNA, samples were thawed and a 10% homogenate prepared by homogenising for 10 seconds at full speed with a UltraTurrax homogeniser. Sample pH was determined and RNA was extracted using guanidine based extraction (TriZOL) and post isolation purification on columns (RNEasy, Qiagen) to remove low molecular weight RNA. RNA quality was determined on the basis of clear 18/26S ribosomal bands using an Agilent Bioanalyzer.

TABLE 1

Anterior Cingulate RNA Samples Extracted for Microarray Analysis

| Sample Number | RIN* | Microarray |
|---|---|---|
| AC1 | 6.5 | Yes |
| AC2 | 6.2 | Yes |
| AC3 | 6.7 | Yes |
| AC4 | 5.5 | No |
| AC5 | 4.6 | No |
| AC6 | 6.3 | Yes |
| AC7 | 4.1 | No |
| AC8 | 6.2 | Yes |
| AC9 | 4.8 | No |
| AC10 | 5.0 | Yes |
| AC11 | 6.5 | Yes |
| AC12 | 4.5 | No |
| AC13 | 7.9 | Yes |
| AC14 | 6.9 | Yes |
| AC15 | 7.2 | Yes |
| AC16 | 7.3 | Yes |
| AC17 | 5.6 | Yes |
| AC18 | 7.3 | Yes |
| AC19 | 5.3 | Yes |
| AC20 | 6.7 | Yes |
| AC21 | 5.9 | Yes |
| AC22 | 6.5 | Yes |
| AC23 | 7.5 | Yes |
| AC24 | 6.8 | Yes |
| AC25 | 7.4 | Yes |
| AC26 | 6.4 | Yes |
| AC27 | 6.2 | Yes |
| AC28 | 5.8 | Yes |
| AC29 | 2.6 | No |
| AC30 | 3.1 | No |
| AC31 | 6.8 | Yes |
| AC32 | 6.8 | Yes |

*RIN = RNA Integrity Number

Samples were subjected to a primary analysis using an Agilent 2100 bioanalyser to provide the RNA integrity number (RIN) to estimate the integrity of total RNA samples. The Agilent 2100 software automatically assigned an integrity number to a eukaryote total RNA sample based on the electrophoretic trace of the sample to indicate the presence or absence of degradation products. On the basis of this primary analysis (see Table 1) samples were taken through two rounds of amplification before placing on Affymetrix Plus 2.0 microarrays.

The initial data screen indicated that 4 cases (samples AC17, AC19, and AC21) were possibly not suitable for further analysis due to low 3'/5' ratios and below average % present calls. Statistical analysis was undertaken to determine if any samples were outliers. Using a Spearmann Rank Correlation approach, three samples provided gene chip results that were outside the main grouping and therefore potential confounders (samples AC17, AC19 and AC21) along with one case which may also be outside the main group (sample AC26). Removal of the outlying samples demonstrated that samples AC17, AC19 and AC21 are possible outliers but that sample AC26 may potentially be retained.

Using both the total dataset and the dataset with samples AC17, AC19 and AC21 filtered out, statistical analysis was undertaken using a stringent and less stringent approach with a maximum of 664 significantly changed genes being identified. Table 2 lists GABAergic receptor genes that were found to be significantly altered in late-onset depression.

TABLE 2

GABAergic genes transcribed in anterior cingulated samples significantly different in subjects with late-onset depression compared with non-depressed subjects

| Fold Change | Gene Name | Map | Description | DEP t-test P-value |
|---|---|---|---|---|
| 1.8 | GABRA1 | 5q34-q35 | gamma-aminobutyric acid (GABA) A receptor, alpha 1 | 0.1204 |

TABLE 2-continued

GABAergic genes transcribed in anterior cingulated samples significantly different in subjects with late-onset depression compared with non-depressed subjects

| Fold Change | Gene Name | Map | Description | DEP t-test P-value |
|---|---|---|---|---|
| 2.1 | GABRA5 | 15q11.2-q12 | gamma-aminobutyric acid (GABA) A receptor, alpha 5 | 0.0 |
| 1.6 | GABRB3 | 15q11.2-q12 | gamma-aminobutyric acid (GABA) A receptor, beta 3 | 0.1029 |
| 0.54 | GABRG1 | 4p12 | gamma-aminobutyric acid (GABA) A receptor, gamma 1 | 0.082 |
| 1.6 | GABRG2 | 5q31.1-q33.1 | gamma-aminobutyric acid (GABA) A receptor, gamma 2 | 0.7756 |
| 2.44 | GABRR1 | 6q14-q21\|6q13-q16.3 | gamma-aminobutyric acid (GABA) A receptor, rho 1 | 0.094 |
| 2.74 | GABBR2 | 9q22.1-q22.3 | gamma-aminobutyric acid (GABA) B receptor, 2 | 0.005 |
| 1.7 | GLRB | 4q31.3 | glycine receptor, beta | 0.0062 |

Example 2

Nuclear Accumbens Transcriptomics

Example 2(i) Sample Selection

Post mortem brain tissue from individuals with late onset depression and individuals without a known neuropsychiatric history has been screened for its suitability for use by assessing pH as a marker of agonal state. Samples from frontal cortex (BA 45) were obtained from storage at −80° C., sub-dissected, thawed and a 10% homogenate (1 gram tissue plus 9 ml water) prepared by homogenising for 10 seconds at full speed with a UltraTurrax homogeniser.

Sample pH was determined using a silver chloride electrode calibrated with aqueous standards.

Example 2(ii) Microarray Analysis

Figure 2:
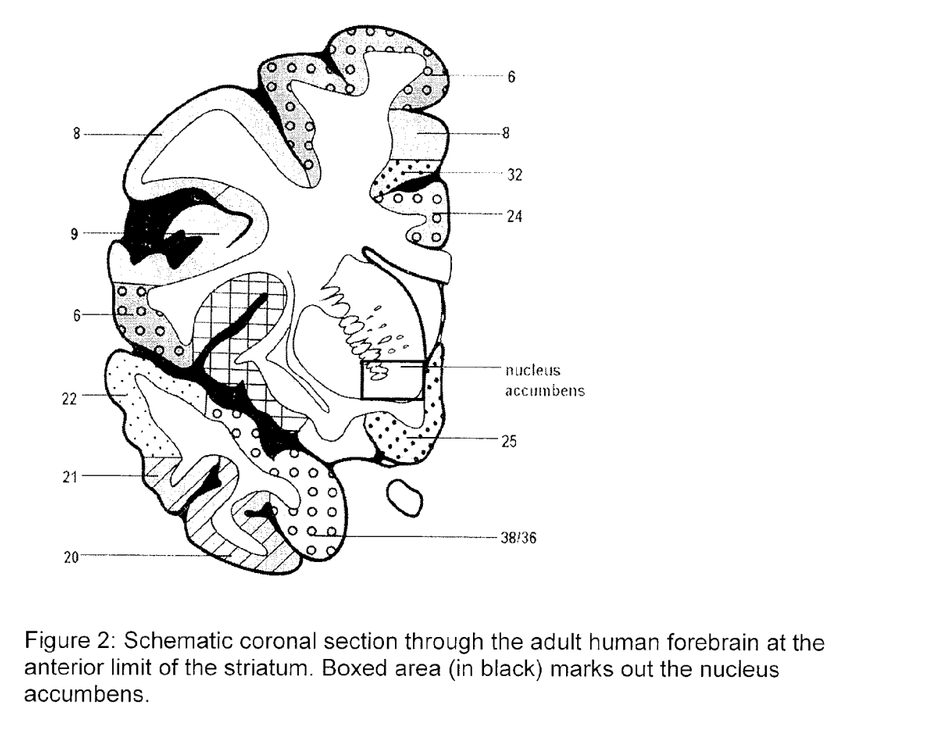
FIG. 2 shows schematic coronal section through the adult human forebrain at the anterior limit of the striatum. Boxed area (in black) marks out the nucleus accumbens.

Following sample selection, a restricted set of samples was available for analysis (see Table 3, below). From this sample set, nucleus accumbens (see FIG. 2) was selected and microdissected at −20° C. These samples were stored frozen at −80° C. and subsequently processed for RNA isolation and microarray analysis.

TABLE 3

Nucleus Accumbens RNA Samples Extracted for Microarray Analysis

| Sample Number | RIN* | Microarray |
|---|---|---|
| NA1 | 8.5 | Yes |
| NA2 | N/A | No |
| NA3 | 6.6 | Yes |
| NA4 | 6.1 | Yes |
| NA5 | 8.7 | Yes |
| NA6 | 8.3 | Yes |
| NA7 | 7.1 | Yes |
| NA8 | 8.1 | Yes |
| NA9 | 7.4 | Yes |
| NA10 | N/A | No |
| NA11 | 6.9 | Yes |
| NA12 | 7.8 | Yes |
| NA13 | 7.9 | Yes |
| NA14 | 7.3 | Yes |
| NA15 | N/A | Yes |
| NA16 | 7.6 | Yes |
| NA17 | 7.7 | Yes |
| NA18 | N/A | No |
| NA19 | 6.7 | Yes |
| NA20 | 8.0 | Yes |
| NA21 | 6.9 | Yes |
| NA22** | 7.0 | Yes |
| NA23 | 6.1 | Yes |
| NA24 | 7.6 | Yes |
| NA25 | 5.9 | No |
| NA26 | 7.8 | Yes |
| NA27 | 7.3 | Yes |
| NA28 | 8.2 | Yes |
| NA29 | 7.4 | Yes |
| NA30 | 6.5 | Yes |
| NA31 | 6.2 | Yes |

*RIN = RNA Integrity Number
**Putamen sample used for comparative purposes for previous anterior cingulate experiment Samples were subjected to a primary analysis using an Agilent 2100 bioanalyser and on the basis of this (see Table 3) samples NA2, NA10, NA18 and NA25 were not processed for further analysis. Other samples were taken through two rounds of amplification before placing on Affymetrix Plus 2.0 microarrays.

From the results of cluster analysis, samples NA20 and NA26 have noticeably different expression patterns to the other samples. These samples also group together in the results of principal component analysis (PCA) analysis. Samples NA20 and NA26 were therefore removed, and the data was re-analysed by hierarchical clustering and PCA.

Using both the dataset with samples NA20 and NA26 filtered out, statistical analysis was undertaken using a stringent and less stringent approach with 121 genes significantly differently expressed in depressed subjects compared with non-depressed subjects. Table 4 lists GABAergic receptor genes that were found to be most significantly altered in late-onset depression.

TABLE 4

GABAergic genes transcribed in nucleus accumbens samples significantly different in subjects with late-onset depression compared with non-depressed subjects

| Fold Change | Gene Name | Map | Description | DEP t-test P-value |
|---|---|---|---|---|
| 1.9 | GABRA1 | 5q34-q35 | gamma-aminobutyric acid (GABA) A receptor, alpha 1 | 0.0003 |
| 0.70 | GABRA4 | 4p12 | gamma-aminobutyric acid (GABA) A receptor, alpha 4 | 0.106 |
| 2.0 | GABRA5 | 15q11.2-q12 | gamma-aminobutyric acid (GABA) A receptor, alpha 5 | 0.0066 |
| 1.6 | GABRB3 | 15q11.2-q12 | gamma-aminobutyric acid (GABA) A receptor, beta 3 | 0.014 |
| 1.6 | GABRG2 | 5q31.1-q33.1 | gamma-aminobutyric acid (GABA) A receptor, gamma 2 | 0.0462 |
| 2.3 | GABRD | 1p\|1p36.3 | gamma-aminobutyric acid (GABA) A receptor, delta | 0.0011 |

TABLE 4-continued

GABAergic genes transcribed in nucleus accumbens samples significantly different in subjects with late-onset depression compared with non-depressed subjects

| Fold Change | Gene Name | Map | Description | DEP t-test P-value |
|---|---|---|---|---|
| 1.8 | GABBR2 | 9q22.1-q22.3 | gamma-aminobutyric acid (GABA) B receptor, 2 | 0 |
| 1.7 | GLRB | 4q31.3 | glycine receptor, beta | 0.0001 |

What is claimed is:

1. An in vivo imaging method for use in the determination of whether a subject has or is predisposed to late-onset depression, said method comprising the steps of:
  (i) administering an in vivo imaging agent to said subject, wherein said in vivo imaging agent comprises a compound that selectively associates with a polynucleotide or polypeptide, said polynucleotide or polypeptide being encoded by a GABAergic receptor gene, and wherein said compound is labelled with an in vivo imaging moiety;
  (ii) allowing said in vivo imaging agent to selectively associate with said polynucleotide and/or said polypeptide expressed in a tissue of said subject;
  (iii) detecting by an in vivo imaging method signals emitted by said in vivo imaging moiety; and,
  (iv) generating an image representative of the location and/or amount of said signals
  wherein said brain tissue is in the anterior cingulate and said GABAergic receptor gene is a gene encoding GABAA receptor subunit γ1 (GABRG1); GABAA receptor subunit ρ1 (GABRR1); or GABAB receptor 2 (GABBR2); or,
  wherein said brain tissue is in the nucleus accumbens and said GABAergic receptor gene is a gene encoding GABAA receptor subunit α4 (GABRA4); GABAA receptor subunit β3 (GABRB3); or GABAA receptor subunit γ2 (GABRG2).

2. The in vivo imaging method as defined in claim 1 wherein said subject is an intact mammalian body in vivo.

3. The in vivo imaging method as defined in claim 1 wherein said brain tissue is in the anterior cingulate and wherein said GABAergic receptor gene is a gene encoding GABBR2 or GABRR1.

4. The in vivo imaging method as defined in claim 1 wherein said brain tissue is in the nucleus accumbens and wherein said GABAergic receptor gene is a gene encoding GABRB3.

5. The in vivo imaging method as defined in claim 1 wherein said in vivo imaging moiety is chosen from:
  (i) a radioactive metal ion;
  (ii) a gamma-emitting radioactive halogen; and,
  (iii) a positron-emitting radioactive non-metal.

6. A method for the diagnosis of late-onset depression comprising:
  (a) in vivo imaging method as defined in claim 1; and,
  (b) comparing the image generated in step (a) with an in vivo image representative of the pattern of uptake of said in vivo imaging agent when said in vivo imaging method is carried out in non-depressed subjects.

* * * * *